United States Patent
Peiro Ibanez

(10) Patent No.: US 10,869,732 B2
(45) Date of Patent: Dec. 22, 2020

(54) SPHERIC ENDO-LUMINAL TRACTION DEVICE FOR ESOPHAGEAL ELONGATION

(71) Applicant: Children's Hospital Medical Center, Cincinnati, OH (US)

(72) Inventor: Jose Peiro Ibanez, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 38 days.

(21) Appl. No.: 15/624,677

(22) Filed: Jun. 15, 2017

(65) Prior Publication Data
US 2017/0360524 A1 Dec. 21, 2017

Related U.S. Application Data

(60) Provisional application No. 62/350,323, filed on Jun. 15, 2016.

(51) Int. Cl.
| | | |
|---|---|---|
| *A61B 90/00* | (2016.01) | |
| *A61B 17/06* | (2006.01) | |
| *A61B 17/04* | (2006.01) | |
| *A61B 17/00* | (2006.01) | |
| *A61B 17/11* | (2006.01) | |

(52) U.S. Cl.
CPC ........ *A61B 90/02* (2016.02); *A61B 17/06166* (2013.01); *A61B 17/1114* (2013.01); *A61B 2017/00818* (2013.01); *A61B 2017/0496* (2013.01); *A61B 2017/1103* (2013.01); *A61B 2017/1132* (2013.01); *A61B 2090/3925* (2016.02); *A61B 2090/3966* (2016.02); *A61B 2217/005* (2013.01)

(58) Field of Classification Search
CPC .......... A61B 90/02; A61B 2018/00488; A61B 17/1114–2017/1117; A61B 2017/00818; A61B 2017/00827; A61B 2017/1132; A61B 2017/1103; A61B 2017/00876; A61B 2017/0496; A61F 2002/044; A61F 5/0036–0046; A61F 5/0069–0089; A61M 39/0247; A61M 2039/0255; A61J 15/0003–0007; A61J 15/0015–0019
See application file for complete search history.

(56) References Cited

U.S. PATENT DOCUMENTS 3,986,493 A * 10/1976 Hendren, III ....... A61B 17/1114
600/12
4,016,721 A 4/1977 Richardson et al.
(Continued)

OTHER PUBLICATIONS

Abraham, Mohan K., et al., "A safer way of suturing in Foker's technique", Journal of Pediatric Surgery, (2013), vol. 48, pp. 1819-1821.
(Continued)

*Primary Examiner* — Katrina M Stransky
*Assistant Examiner* — Brigid K Byrd
(74) *Attorney, Agent, or Firm* — Faegre Drinker Biddle & Reath LLP

(57) ABSTRACT

Methods and apparatuses for applying tensile force to one or more tissue regions within a body. Illustratively, an implant ball including a spherical side wall is received within a tubular organ, and tensile sutures extend through the implant ball for applying a tensile force to facilitate elongation of the tubular organ.

24 Claims, 15 Drawing Sheets

(56) References Cited

U.S. PATENT DOCUMENTS

| | | | |
|---|---|---|---|
| 5,558,665 A | 9/1996 | Kieturakis | |
| 6,067,990 A | 5/2000 | Kieturakis | |
| 6,723,053 B2 | 4/2004 | Ackerman et al. | |
| 2006/0217762 A1* | 9/2006 | Maahs | A61B 17/0401 606/213 |
| 2007/0049954 A1* | 3/2007 | Caty | A61B 17/0643 606/153 |
| 2008/0091235 A1* | 4/2008 | Sirota | A61B 17/0057 606/215 |
| 2010/0106194 A1* | 4/2010 | Bonutti | A61B 17/17 606/279 |
| 2014/0194805 A1* | 7/2014 | Levine | A61B 17/0401 604/8 |
| 2015/0342609 A1 | 12/2015 | DuPont et al. | |
| 2016/0114116 A1* | 4/2016 | Evans | A61M 16/0404 128/207.15 |
| 2017/0095363 A1* | 4/2017 | Hiernaux | A61B 17/0401 |
| 2018/0368835 A1* | 12/2018 | Berberich | A61B 17/0401 |

OTHER PUBLICATIONS

Anuntkosol, Maitree, M.D., et al., "Gastric Transposition for Infants with Long-Gap Esophageal Atresia", The Thai Journal of Surgery (2005), vol. 26, pp. 127-132.

Bagolan, P., et al., "Long Gap Esophageal Atresia and Esophageal Replacement: Moving Toward a Separation?", Journal of Pediatric Surgery, vol. 39, No. 7, Jul. 2004, pp. 1084-1090.

Bagolan, P., et al., "Long-gap esophageal atresia: traction-growth and anastomosis—before and beyond", Diseases of the Esophagus, vol. 26, (2013), pp. 372-379.

Bonfield, Tracey L, et al., "Peroxisome Proliferator-Activated Receptor-γ Is Deficient in Alveolar Macrophages from Patients with Alveolar Proteinosis", Am. J. Respir. Cell Mol. Biol., vol. 29. (2003), pp. 677-682.

Cavelier, Clara, et al., "Lipid efflux by the ATP-binding cassette transporters ABCA1 and ABCG1", Biochimica et Biophysica Acta 1761 (2006) pp. 655-666, available online at www.sciencedirect.com.

Daniels, Christopher B., et al., "Body Temperature Alters the Lipid Composition of Pulmonary Surfactant in the Lizard *Ctenophorus nuchalis*", Experimental Lung Research, vol. 16, (1990), pp. 435-449, Copyright © by Hemisphere Publishing Corporation.

De Jong, Elizabeth M., et al., "Etiology of Esophageal Atresia and Tracheoesophageal Fistula: "Mind the Gap"", Curr Gastroenterol Rep, (2010), vol. 12, pp. 215-222.

Ditiatkovski, Michael, et al., "GM-CSF Deficiency Reduces Macrophage PPAR-γ Expression and Aggravates Atherosclerosis in ApoE-Deficient Mice", Arterioscler Thromb Vasc Biol., Oct. 2006, 17 pages.

Foker, John E., M.D. et al., "Development of a True Primary Repair for the Full Spectrum of Esophageal Atresia", Annals of Surgery, vol. 226, No. 4, pp. 533-543, Oct. 1997.

Foker, John E., M.D., et al., "Long-gap esophageal atresia treated by growth induction: the biological potential and early follow up results", Seminars in Pediatric Surgery, (2009), vol. 18, pp. 23-29.

Forbes, Amy, et al., "Alveolar macrophage depletion is associated with increased surfactant pool sizes in adult rats", J Appl Physiol, vol. 103, (2007), pp. 637-645.

Friedmacher, Florian, "Delayed primary anastomosis for management of long-gap esophageal atresia: a meta-analysis of complications and long-term outcome", Pediatr Surg Int, vol. 28, (2012), pp. 889-906.

Griese, M., "Pulmonary surfactant in health and human lung diseases: state of the art", Eur Respir J. (1999), vol. 13, pp. 1455-1476.

Gurel, Okyanus, et al., "Macrophage and type II cell catabolism of SP-A and saturated phosphatidylcholine in mouse lungs"; Am J Physiol Lung Cell Mol Physiol, vol. 208, (2001), pp. L1266-L1272.

Hadidi, Ahmed T., et al., "Long gap esophageal atresia: lengthening technique and primary anastomdsis", Journal of Pediatric Surgery, vol. 42, (2007), pp. 1659-1662.

Holland, Andrew J.A., et al., "Surgical outcomes of esophageal atresia without fistula for 24 years at a single institution", Journal of Pediatric Surgery, vol. 44, (2009), pp. 1928-1932.

Igarashi, Masaki, et al., "The Critical Role of Neutral Cholesterol Ester Hydrolase 1 in Cholesterol Removal From Human Macrophages", Circulation Research, Nov. 26, 2010, 32 pages.

Okazaki, Hiroaki, et al., "Identification of Neutral Cholesterol Ester Hydrolase, a Key Enzyme Removing Cholesterol from Macrophages", The Journal of Biological Chemistry, vol. 283, No. 48, Nov. 28, 2008, pp. 33357-33364.

Thomassen, Mary Jane, et al., "ABCG1 is deficient in alveolar macrophages of GM-CSF knockout mice and patients with pulmonary alveolar proteinosis", Journal of Lipid Research, vol. 48, (2007), pp. 2762-2768.

Liszewski, Mark C., et al., "Imaging of long gap esophageal atresia and the Foker process: expected finding and complications," Pediatr. Radiol. (2014) vol. 44, pp. 467-475.

Livaditis, Alexander, et al., "Esophageal End-To-End Anastomosis", Scand J. Thor Cardiovasc Surg, vol. 6, (1972), pp. 206-214.

Lopes, Maria Francelina, et al., "Very Long Gap Esophageal Atresia Successfully Treated by Esophageal Lengthening Using External Traction Sutures", Journal of Pediatric Surgery, vol. 39, No. 8, Aug. 2004, pp. 1286-1287.

Louhimo Ilmo, et al., "Esophageal Atresia: Primary Results of 500 Consecutively Treated Patients", Journal of Pediatric Surgery, vol. 18, No. 3, Jun. 1983, 13 pages.

Macksood, Daniel J. M.D., et al., "Complications after gastric transposition in children", Canadian Association of Radiologists Journal., vol. 48, No. 4, Aug. 1997, pp. 259-264.

Mochizuki, Kyoko, et al., "A modified Foker's technique for long gap esophageal atresia", Pediatr Surg Int, vol. 28, (2012), pp. 851-864.

Myers, N.A., et al., "Oesophageal atresia without fistula—anastomosis or replacement?", Pediatric Surg Int, vol. 2, (1987), pp. 216-222.

Nasr, Ahmed, et al., "Mechanical Traction Techniques for Long-Gap Esophageal Atresia: A Critical Appraisal", Eur J Pediatric Surg, vol. 23, (2013), pp. 191-197.

Quimet, Mireille, et al., "Autophagy Regulates Cholesterol Efflux from Macrophage Foam Cells via Lysosomal Acid Lipase", Cell Metabolism, vol. 13, Jun. 8, 2011, pp. 655-667.

Pinheiro, Paul Fernando Martins, et al., "Current knowledge on esophageal atresia", World Journal of Gastroenterology, vol. 18, No. 28, Jul. 28, 2012, pp. 3662-3672.

Postlethwait, R.W., M.D., "Colonic Interposition for Esophageal Substitution", Surgery, Gynecology & Obstetrics, vol. 156, Mar. 1983, 7 pages.

Al-Qahtani, Aayed R., et al., "Lengthening Technique for Long Gap Esophageal Atresia and Early Anastomosis", Journal of Pediatric Surgery, vol. 38, No. 5, May 2003, pp. 737-739.

Ramirez-Zacarias, J. L., et al., "Quantitation of adipose conversion and triglycerides by staining intracytoplasmic lipids with Oil red O", Histochemistry, vol. 97, (1992), pp. 493-497.

Ron, Ori et al., "The surgical approach to esophageal atresia repair and the management of long-gap atresia: results of a survey", Seminars in Pediatric Surgery, vol. 18, (2009), pp. 44-49.

Sherman, Charles D., Jr., et al., "Oesophageal Reconstruction in Children Using Intrathoracic Colon", Downloaded from http://adc.bmj.com/ on Apr. 6, 2017—Published by group.bmj.com, 8 pages.

Spitz, Lewis, "Gastric Transposition for Esophageal Substitution in Children", Journal of Pediatric Surgery, vol. 27, No. 2, Feb. 1992, pp. 252-259.

Spitz, Lewis, "Esophageal Atresia: Past, Present, and Future", Journal of Pediatric Surgery, vol. 31, No. 1, Jan. 1996, pp. 19-25.

Spitz, L., et al., Long-gap oesophageal atresia, Pediatr Surg Int, vol. 11, (1996), pp. 462-465.

Spitz, Lewis, "Esophageal Atresia: Lessons I have learned in a 40-year experience", Journal of Pediatric Surgery, vol. 41, (2006), pp. 1635-1640.

(56) References Cited

OTHER PUBLICATIONS

Sroka, Mariusz, et al., "The Foker Technique (FT) and Kimura Advancement (KA) for the Treatment of Children with Long-Gap Esophageal Atresia (LGEA): Lessons Learned at Two European Centers", Eur J Pediatr Surg, vol. 23, (2013), pp. 3-7.

Takamizawa, Shigeru et al., "Multistaged esophageal elongation technique for long gap esophageal atresia: experience with 7 cases at a single institute", Journal of Pediatric Surgery, vol. 40, (2005), pp. 781-784.

Van Der Zee, David C., et al., "Thoracoscopic traction technique in long gap esophageal atresia: entering a new era", Surg Endosc, vol. 29, (2015), pp. 3324-3330.

* cited by examiner

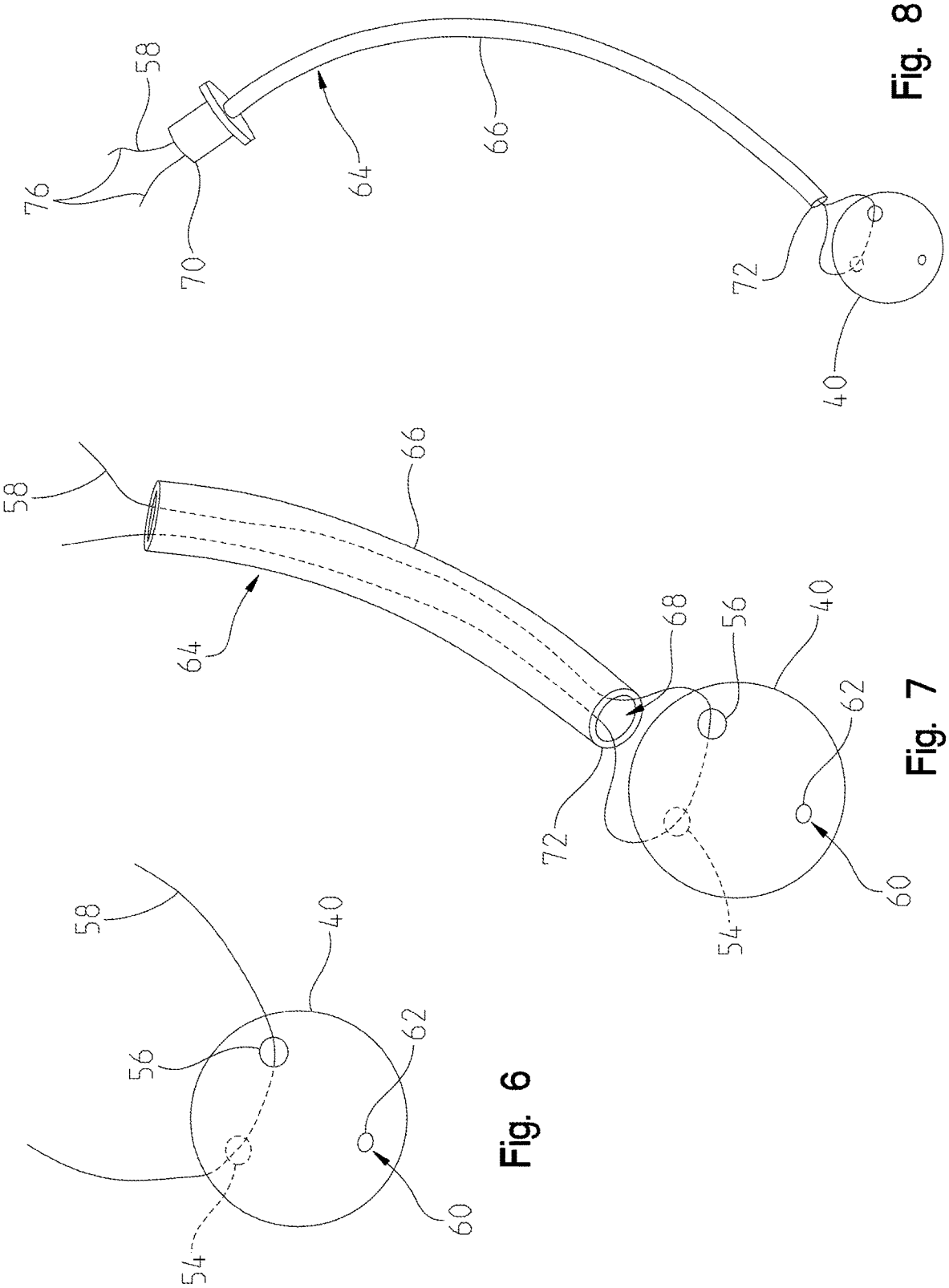

SPHERIC ENDO-LUMINAL TRACTION DEVICE FOR ESOPHAGEAL ELONGATION

CROSS-REFERENCE TO RELATED APPLICATION

The present application claims priority to U.S. Provisional Patent Application Ser. No. 62/350,323, filed Jun. 15, 2016, the disclosure of which is expressly incorporated herein by reference.

BACKGROUND AND SUMMARY OF THE DISCLOSURE

The present disclosure relates generally to apparatuses and methods for applying tensile force to tissue regions of a body and, more particularly, to apparatuses and methods for applying tensile force to elongate tubular organs. An illustrative apparatus and method is configured to address conditions of long gap esophageal atresia (LGEA) by facilitating esophageal elongation by stretching by utilizing a spheric endo-luminal traction device.

Esophageal atresia (EA) is the most common congenital esophageal defect (occurring in about 1 out of 4000 births). Esophageal atresia (EA) is a medical condition where a portion of the esophagus has not developed and is missing. More particularly, it is an abnormal development with a blockage of the esophagus continuity and the formation of a proximal esophagus pouch and a distal esophagus pouch, sometimes combined with a tracheoesophageal fistula (TEF). Neonates suffering from EA are not able to eat until restoring the continuity of the esophagus with surgical intervention.

The gap between the two separated proximal and distal esophagus pouches can be relative small or large. In the later case, defined as "long gap" esophageal atresia (LGEA), it may be difficult to perform a direct anastomosis. While "long gap" is not strictly defined, clinical surgeons often define it by two criteria. Long gap may be defined if (1) the gap is larger than about 3 centimeters, and (2) surgeons could not likely perform a primary repair directly to bridge the spaced apart esophagus pouches. Hence, different surgical techniques have been developed to make the esophagus pouches get closer, and then do an anastomosis. However, this is still a major challenge in pediatric surgery.

More particularly, long-gap esophageal atresia (LGEA) is still a major surgical challenge. Options for esophageal reconstruction include the use of native esophagus or esophageal replacement with stomach, colon, or small intestine. Nonetheless, there is a consensus among most pediatric surgeons that the preservation of the native esophagus is associated with better postoperative outcomes. Thus, every effort should be made to conserve the native esophagus.

Besides esophageal replacement, the use of the esophagus itself seems to be an objective. Techniques have been designed for esophageal elongation by stretching through the use of applying a tensile force. However, detachment of the sutures before complete elongation is a common complication.

Esophageal atresia (or oesophageal atresia) is a congenital medical condition (birth defect) that affects the alimentary tract. It causes the esophagus to end in a blind-ended pouch rather than connecting normally to the stomach. It comprises a variety of congenital anatomic defects that are caused by an abnormal embryological development of the esophagus. It is characterized anatomically by a congenital obstruction of the esophagus with interruption of the continuity of the esophageal wall.

This condition takes several different forms, often involving one or more fistulas connecting the trachea to the esophagus (tracheoesophageal fistula). Type A is often called "long gap", "pure" or "isolated" esophageal atresia, which is characterized by the a "gap" between two esophageal blind pouches with no fistula present. Type B is often referred to as esophageal atresia with proximal TEF (tracheoesophageal fistula), where the upper esophageal pouch connects abnormally to the trachea, and the lower esophageal pouch ends blindly. Type C is typically called esophageal atresia with distal TEF (tracheoesophageal fistula), where the lower esophageal pouch connects abnormally to the trachea, and the upper esophageal pouch ends blindly. Type D is typically referred to as esophageal atresia with both proximal and distal TEFs (two tracheoesophageal fistulas), where both the upper and lower esophageal pouches make abnormal connections with the trachea in two separate, isolated locations.

Common treatment for esophageal atresia may involve connecting the two end segments of the esophagus to each other. This may be accomplished through a series of incisions between the ribs on the right of the patient and mechanically manipulating the proximal and distal segments or pouches of the esophagus as to ultimately join them together through surgical anastomosis. In some cases of long-gap esophageal atresia (LGEA), the gap between the proximal and distal esophageal pouches may be excessive (e.g., greater than 3 cm long) and cannot be corrected during a simple surgery. In long-gap esophageal atresia (LGEA), various surgical approaches have been used, such as removal and insertion of another digestive segment of the patient, such as the colon.

A commonly used advanced surgical treatment call the Foker method has been used to elongate and then join together the spaced apart esophageal pouches, typically when the patient is at 3 months of age or older. In the Foker method, surgeons illustratively stitch traction sutures into the spaced apart esophageal pouches at respective locations. The sutures may be wrapped around the ribs, which are used as pulleys, and tied off outside of the back of the patient. The suture loops may be tightened daily so as to cause stretching or growth of the respective esophageal pouches until the ends are close enough to be joined together.

The Foker technique is currently the most applied procedure for the repair in the neonatal period of EA. But surgeons still face many difficulties, such as the wide variety of gap length, stricture caused by rapid growth, tissue cutting or tearing by sutures, and the sedation condition of the infant during treatment. The main complication of the Foker technique is tissue cutting through the esophagus by sutures during the period of esophagus traction. If the sutures are outstretched, the patient would need to receive an additional thoracotomy for reconnecting the sutures with the esophagus.

In the present disclosure, apparatuses and methods have been developed to improve the outcomes of the conventional Foker technique. The outcomes of these new apparatuses and methods were assessed by an in-vitro ex-vivo model. Five modified suturing methods (2 extra luminal and 3 intra luminal) were proposed to compare with the original Foker's suturing method (control group). The objectives of the new apparatuses and methods were to provide better performance for traction with less potential complications.

According to an illustrative embodiment of the present disclosure, a system for lengthening a tubular organ by applying tensile force includes a first implant configured to be received within a first pouch of the tubular organ, the first implant including an arcuate outer surface. A first tension suture extends through the first implant. An insertion device is configured to place the first implant within the first pouch, the insertion device including a proximal end and a distal end. A coupler is configured to releasably couple the first implant to the distal end of the insertion device. Tensile force applied to the first tension suture causes the first pouch to elongate. In an illustrative embodiment, the first implant includes a ball including a side wall defining an internal chamber and a spherical outer surface.

In a further illustrative embodiment of the present disclosure, a second implant is configured to be received within a second pouch of the tubular organ, the second implant including an arcuate outer surface. A second tension suture extends through the second implant. Tensile force applied to the first tension suture and the second tension suture cause the first pouch and the second pouch to elongate toward each other. In an illustrative embodiment, the second implant includes a ball including a side wall defining an internal chamber and a spherical outer surface.

According to another illustrative embodiment of the present disclosure, an implant for lengthening a tubular organ by applying tensile force includes a ball having a side wall defining an internal chamber and a spherical outer surface, the ball being formed of a polymer and having a fixed outer diameter of between 5 millimeters and 15 millimeters. A tension suture extends through a first location in the side wall of the ball, the internal chamber of the ball, and a second location in the side wall of the ball. Tensile force applied to the tension suture causes a semi-spherical distribution of force.

According to a further illustrative embodiment of the present disclosure, a method of lengthening a tubular organ by applying tensile force includes the steps of coupling a proximal implant ball to the distal end of an insertion tube, and inserting the insertion tube into the esophagus of a patient. The method further includes the steps of placing the proximal implant ball into a proximal pouch of the esophagus, inserting a tension suture through the proximal implant ball, and applying successive tensile force to the proximal implant ball through the tension suture to elongate the proximal pouch of the esophagus. In a further illustrative embodiment, the method includes the steps of placing a distal implant ball into a distal pouch of the esophagus, inserting a tension suture through the distal implant ball, and applying successive tensile force to the distal implant ball through the tension suture to elongate the distal pouch of the esophagus.

Additional features and advantages of the present invention will become apparent to those skilled in the art upon consideration of the following detailed description of the illustrative embodiments exemplifying the best mode of carrying out the invention as presently perceived.

BRIEF DESCRIPTION OF THE DRAWINGS

The detailed description of the drawings particularly refers to the accompanying figures in which:

FIG. 6 is a perspective view of the ball of FIG. 4, showing a placement suture passing through openings within the side wall;

FIG. 7 is a perspective view of a tube receiving the placement suture for coupling the implant ball of FIG. 6 to the tube;

FIG. 8 is a perspective view of the assembly of FIG. 7;

DETAILED DESCRIPTION OF THE DRAWINGS

The embodiments of the invention described herein are not intended to be exhaustive or to limit the invention to precise forms disclosed. Rather, the embodiments elected for description have been chosen to enable one skilled in the art to practice the invention.

Esophageal Atresia

Figure 1A:
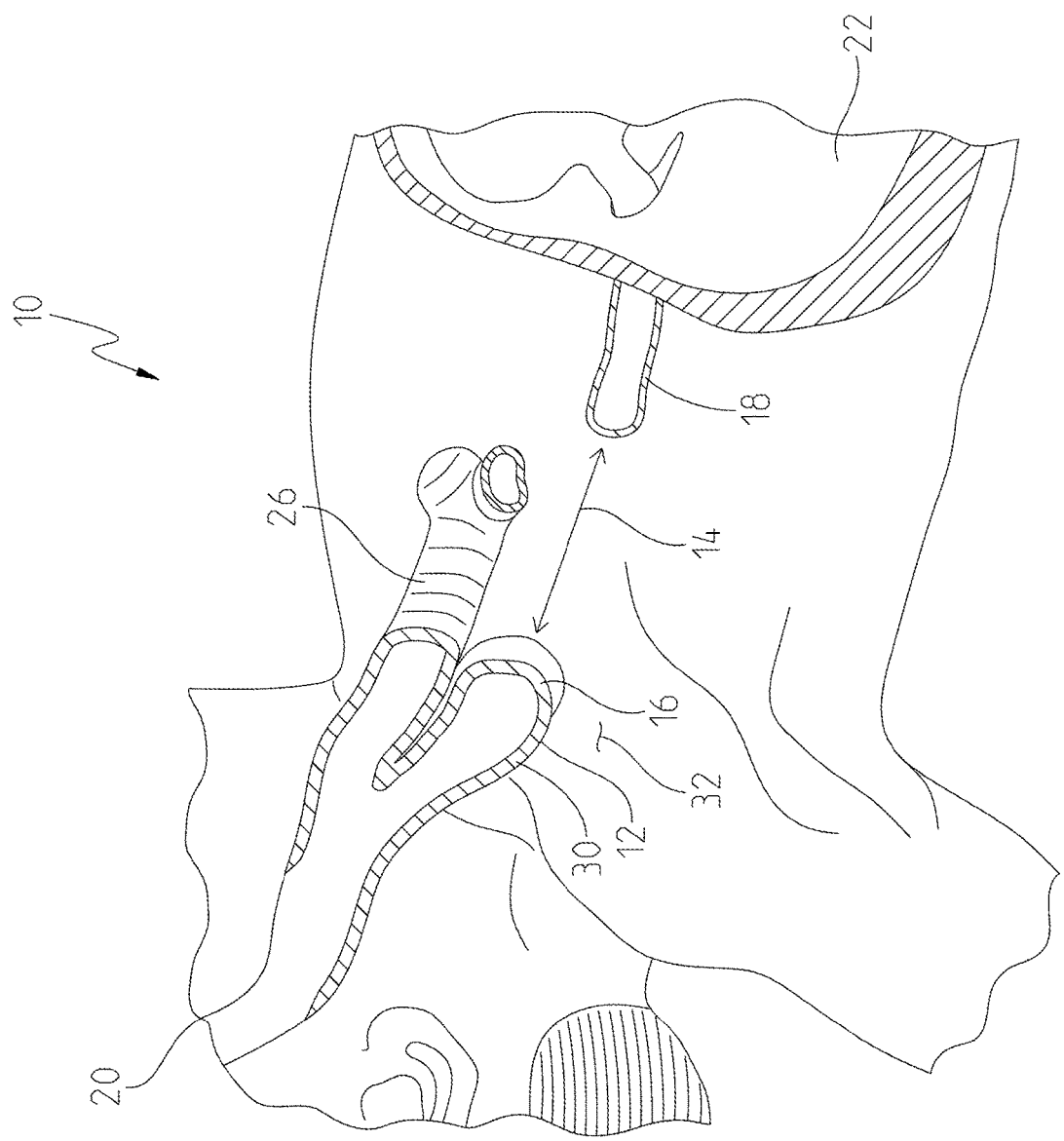
FIG. 1A is a perspective view, in partial cross-section, showing a first long-gap esophageal elongation condition.
Figure 1B:
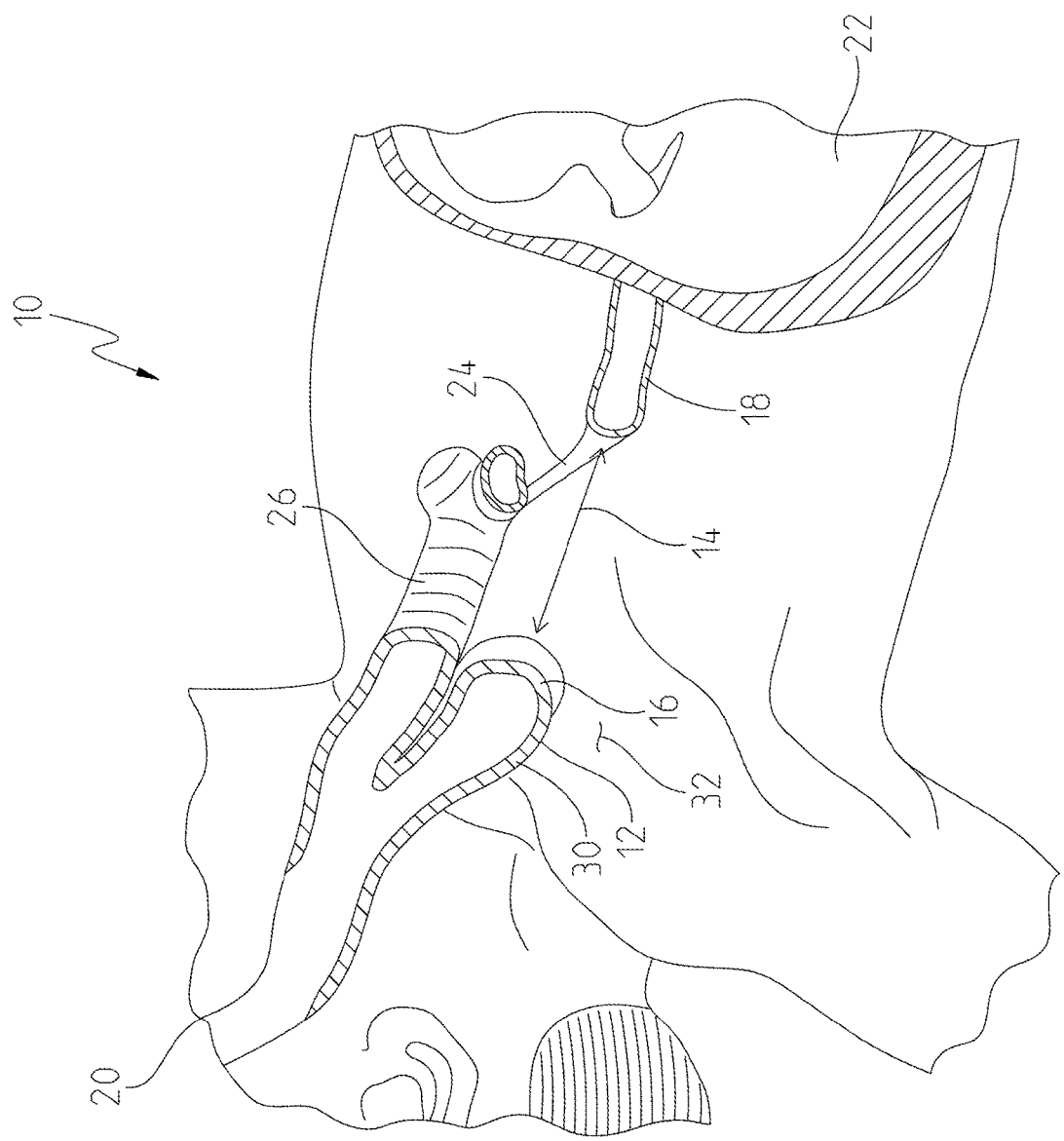
FIG. 1B is a perspective view, in partial cross-section, showing a second long-gap esophageal elongation condition.

Referring initially to FIGS. 1A and 1B, a patient 10, illustratively an infant or neonate, is shown as including an esophageal atresia (EA) condition. More particularly, the esophagus 12 of the patient 10 is separated by a gap 14.

Illustratively, the esophagus 12 is split into an upper or proximal esophagus portion or pouch 16, and a lower or distal esophagus portion or pouch 18, thereby failing to provide a continuous passageway from the oral cavity or mouth 20 to the stomach 22. As further detailed above, long gap esophageal atresia (LGEA) may be defined if (1) the gap 14 is larger than about 3 centimeters, and (2) surgeons could not likely perform a primary repair directly to bridge the proximal and distal esophagus pouches 16 and 18.

FIG. 1A illustrates type A LGEA, often called "long gap", "pure" or "isolated" esophageal atresia, which is characterized by the gap 14 positioned between two esophageal blind pouches 16 and 18 with no fistula present. FIG. 1B illustrates type C LGEA, often referred to as esophageal atresia with a distal tracheoesophageal fistula (TEF) 24, where the distal esophagus pouch 18 connects abnormally to the trachea 26, and the proximal esophagus pouch 16 ends blindly.

While types A and C LGEA are illustrated, it should be appreciated that the apparatuses and methods of the present disclosure may be used with other types of EA (including, for example, types B and D). As further noted herein, type B is typically called esophageal atresia with proximal tracheoesophageal fistula (TEF), where the proximal esophagus pouch 16 connects abnormally to the trachea 26, and the distal esophagus pouch 18 ends blindly. As also further detailed herein, type D is typically referred to as esophageal atresia with both proximal and distal tracheoesophageal fistulas (two TEFs), where both the proximal and distal esophageal pouches 16 and 18 make abnormal connections with the trachea 26 in two separate, isolated locations.

While the following description details apparatuses and methods for the elongation of esophagus pouches, it should be appreciated that the invention may be used with other tubular organs. For example, the apparatuses and methods of the present disclosure may be used to lengthen an intestine in short bowel syndrome, to lengthen a bladder for bladder augmentation, and to lengthen other pouches or tubular structures within tissue regions of a body.

Extra Luminal Apparatuses and Methods

Figure 2C:
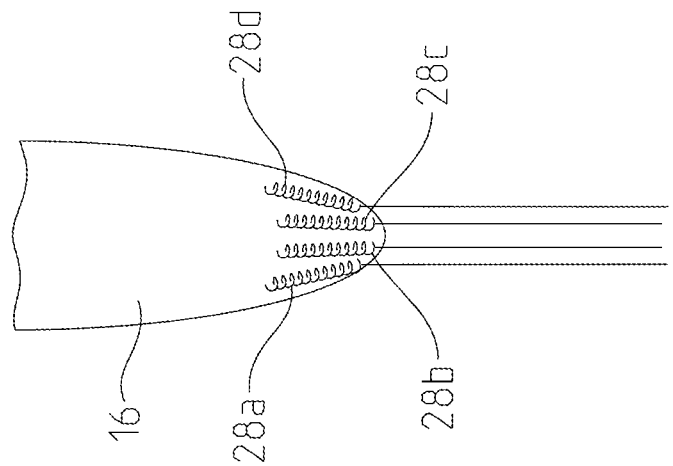
FIG. 2C is a diagrammatic view of an extra luminal spiral method of applying tensile force to an esophagus pouch.
Figure 2B:
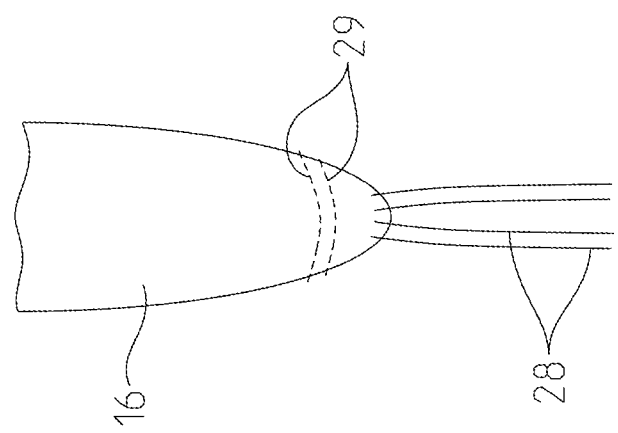
FIG. 2B is a diagrammatic view of an extra luminal purse string method of applying tensile force to an esophagus pouch.
Figure 2A:
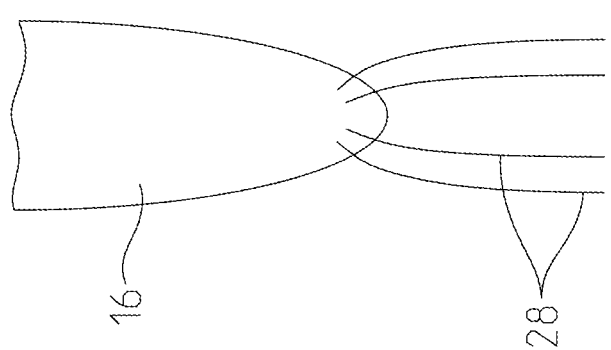
FIG. 2A is a diagrammatic view of an extra luminal Foker method of applying tensile force to an esophagus pouch.

FIGS. 2A-2C illustrate various extra luminal apparatuses and methods for applying tensile force to an esophagus pouch. In the following description of FIGS. 2A-2C, reference will be made to the proximal esophagus pouch 16. However, it may be appreciated that a similar configuration may be utilized with the distal esophagus pouch 18.

FIG. 2A shows a conventional Foker apparatus and method using mechanical stimulations to accelerate the growth of at least one of the proximal and distal esophagus pouches 16 and 18. Once the patient 10 is diagnosed with LGEA, surgeons will assess the circumstance and perform a Foker technique. Illustratively, surgeons will perform a thoracotomy and sew at least two tension stitches or sutures 28 on the proximal esophagus pouch 16. The tension sutures 28 are illustratively stretched out through incisions in the esophagus wall 30 and the thoracic wall 32.

Illustratively, the patient 10 is under sedation, and the tension sutures 28 are fixed with cotton rolls (not shown) and gradually pulled out between 1 millimeter and 2 millimeters per day. After approximately two weeks, if and when the esophagus pouch 16 has stretched or grown to a sufficient length, surgeons perform another thoracotomy to connect the proximal and distal esophagus pouches 16 and 18 together.

As noted above, the Foker method presents difficulties, such as the wide variety of gap length, stricture caused by rapid growth, tissue cutting by the sutures, and the sedation condition of the patient during the entire treatment. The main complication of this technique is the tissue cutting through the esophagus by the tensile sutures during the period of esophagus traction. If the sutures are outstretched, the patient would require an additional thoracotomy for reconnecting the sutures with the esophagus, an additional potential risk to the neonate.

FIG. 2B shows a purse string apparatus and method, where tension sutures 28 extend into the esophagus pouch 16 and then are stitched circumferentially around the pouch 16. More particularly, the tension sutures 28 are placed in a circle 29 a few millimeters from the end of the pouch 16. As such, the tension sutures 28 bite additional esophagus tissue than the Foker method of FIG. 2A.

FIG. 2C shows a spiral apparatus and method, where the tensile sutures 28 extend into the esophagus pouch 16 and then are each spiral is stitched along a longitudinal axis. More particularly, a plurality of spiral tension sutures 28a, 28b, 28c, 28d extend substantially parallel to the longitudinal axis of the pouch 16, 18, each spiral tension suture 28 having a length of about 1 centimeter. As such, the tension sutures 28 bite additional esophagus tissue that the Foker method of FIG. 2A.

Intra Luminal Apparatuses and Methods

Figure 3C:
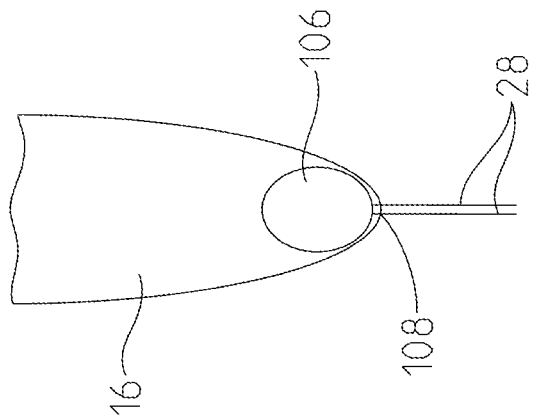
FIG. 3C is a diagrammatic view of an intra luminal method of applying tensile force to an esophagus pouch, wherein sutures are coupled to an inflatable balloon disposed within the pouch.
Figure 3B:
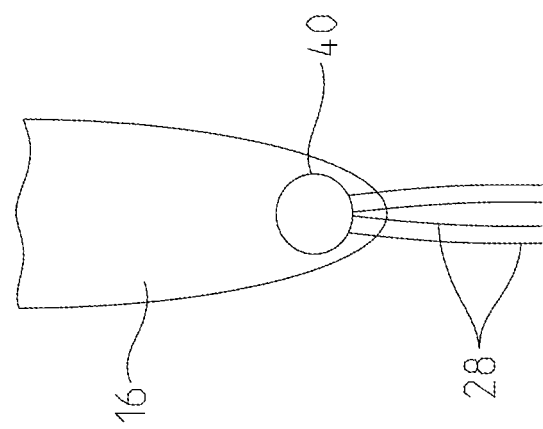
FIG. 3B is a diagrammatic view of an intra luminal method of applying tensile force to an esophagus pouch, wherein sutures are coupled to a spherical ball within the pouch.
Figure 3A:
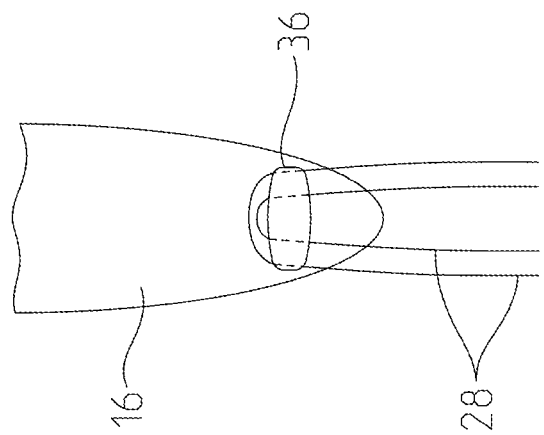
FIG. 3A is a diagrammatic view of an intra luminal method of applying tensile force to an esophagus pouch, wherein sutures are coupled to a button disposed within the pouch.

FIGS. 3A-3C illustrate various intra luminal apparatuses and methods for applying tensile force to an esophagus pouch. In the following description of FIGS. 2A-2C, reference will be made to the proximal esophagus pouch 16. However, it may be appreciated that a similar configuration may be utilized with the distal esophagus pouch 18.

FIG. 3A shows an apparatus and method wherein tensile sutures 28 are coupled to an implant disk or button 36 disposed within the esophagus pouch 16. The button 36 is illustratively formed of a polymer, such as silicone (rubber) or polytetrafluoroethylene (PTFE), and has a diameter of about 5 millimeters and a thickness of about 3 millimeters. The button 36 is placed within the esophagus pouch 16, and then fixed with the tension sutures 28 extending though the esophagus wall 30 and the thoracic wall 32.

FIG. 3B shows an apparatus and method wherein tensile sutures 28 are coupled to a first or proximal implant ball 40 disposed within the esophagus pouch 16, 18. As further detailed herein, the implant ball 40 includes a side wall 42 having an outer spherical surface 44. The side wall 42 is illustratively formed of a polymer, such as silicone (rubber) or polytetrafluoroethylene (PTFE), and defines an internal chamber 46. Illustratively, the outer diameter of the ball 40 is between 5 millimeters and 10 millimeters. In one illustrative embodiment, the ball 40 has an outer diameter of approximately 8 millimeters. The ball 40 is placed within the esophagus pouch 16, and is then fixed with the tension sutures 28 extending through the esophagus wall 30 and the thoracic wall 32.

Figure 4:
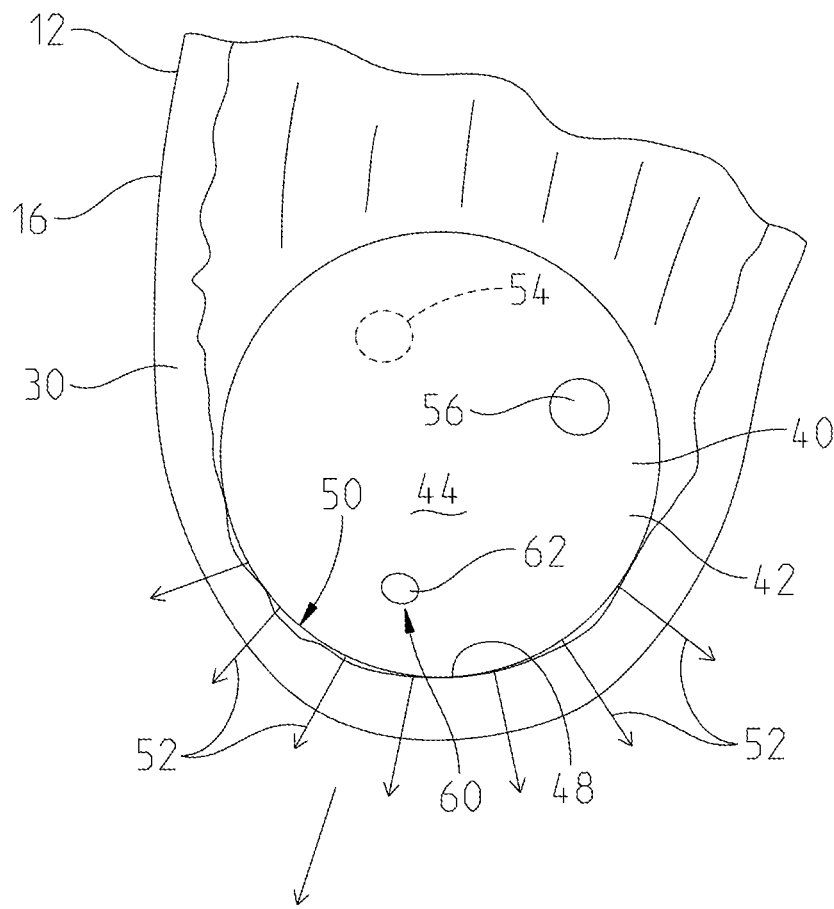
FIG. 4 is a side elevational view of an implant ball received within an esophagus pouch.

As shown in FIG. 4, the outer spherical surface 44 of the implant ball 40 facilitates an expanded distribution of force. More particularly, the outer spherical surface 44 is configured to distribute the vectors of traction forces over an expanded surface area 48 of the intraluminal pouch concavity 50 (as represented by arrows 52). Illustratively, a first opening 54 and a second opening 56 are formed within the side wall 42 and are configured to receive a placement suture 58.

Figure 5:
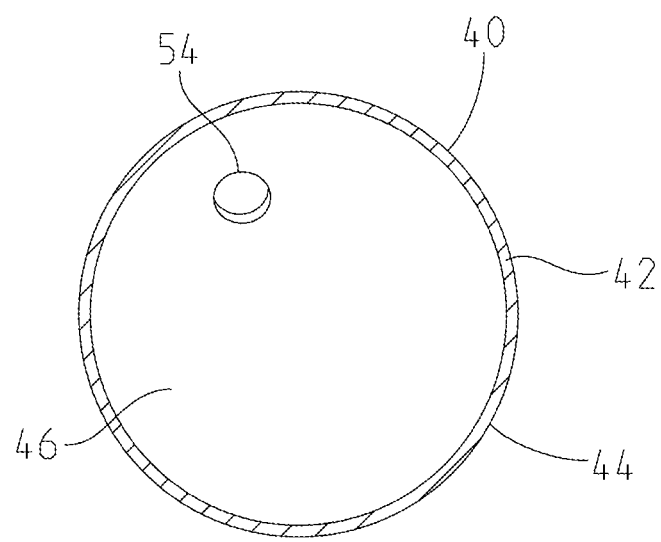
FIG. 5 is a vertical cross-sectional view of the implant ball of FIG. 4.

With further reference to FIGS. 4 and 5, the implant ball 40 illustratively includes a marker element 60 for at least one of radiology and ultrasonic detection to assess position of the ball 40 and monitor lengthening of the esophagus pouch 16, 18. In one illustrative embodiment, the marker element 60 is a radiopaque element including an internal radiopaque particle 62. In another illustrative embodiment, the marker element 60 is a radiopaque substance coating on the outer spherical surface 44. The internal radiopaque particle 62 may comprise a metallic or radiopaque polymer particle inserted (e.g., molded) within the side wall 42 of the ball 40. The radiopaque substance coating may any one of gold, platinum and tantalum coatings. Alternatively, the entire side wall 42 may be formed of a radiopaque material (e.g., polymer including an additive or filler material opaque to x-rays). For example, radiopaque additives may be barium sulfate, bismuth, and/or tungsten.

In certain illustrative embodiments, the side wall 42 of the implant ball 40 may be coated with nanoparticles for the slow release of substances, such as drugs and/or medications. Such substances may comprise anti-inflammatory agents, growth factors, etc.

With reference to FIGS. 6-8, the placement suture 58 illustratively extends through the first opening 54 of the side wall 42, the internal chamber 46, and the second opening 56 of the side wall 42. An insertion device 64 may be used to place the implant ball 40 within the esophagus pouch 16. Illustratively, the insertion device 64 includes an insertion tube 66 having a longitudinal passageway or lumen 68 extending between a proximal end 70 and a distal end 72. The distal end 72 of the tube 66 may be coupled to the ball 40.

Figure 9:
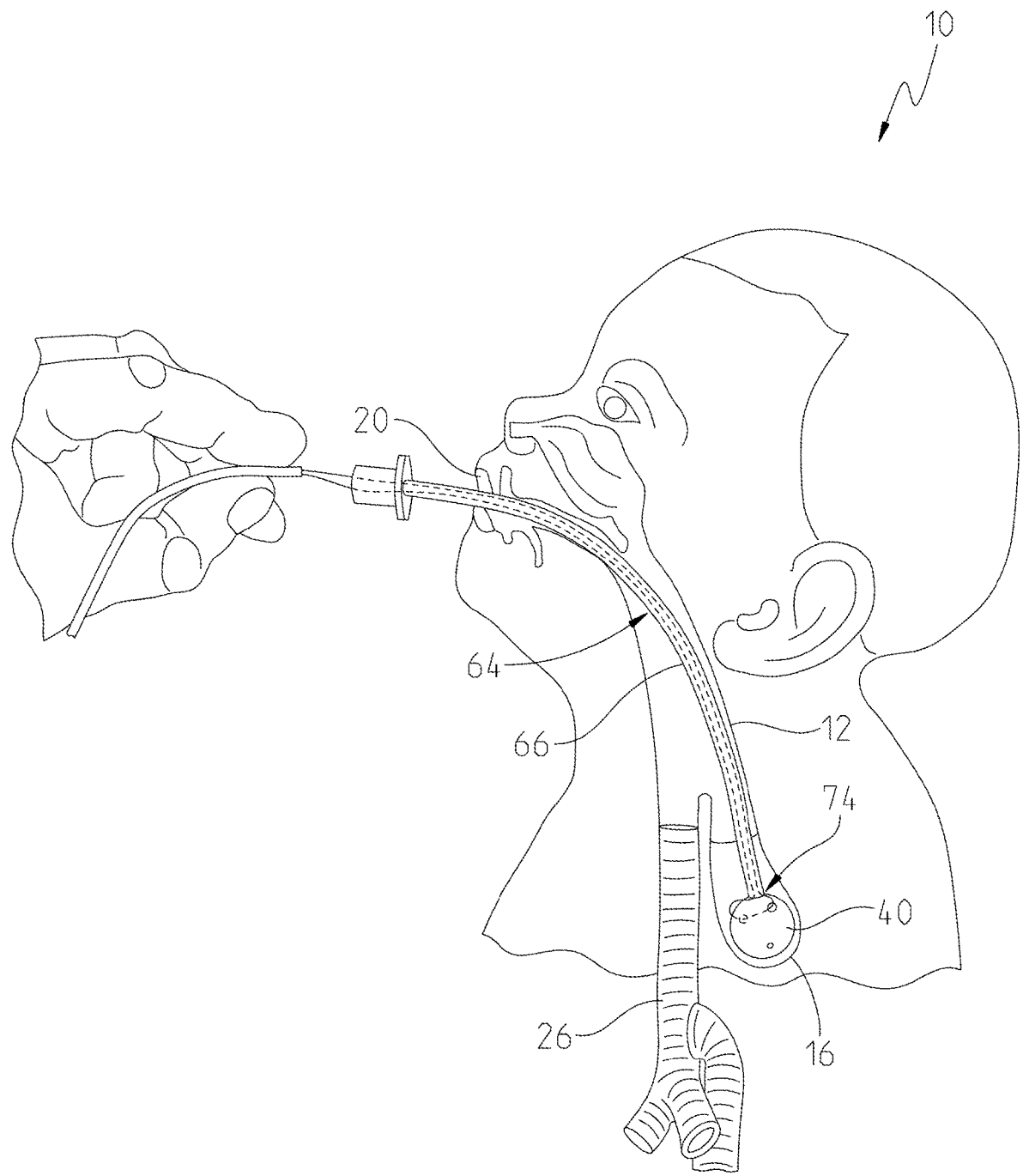
FIG. 9 is a view of the assembly of FIG. 8, shown received within the proximal esophagus pouch of the patient.

In the illustrative embodiment of FIG. 9, a coupler 74 is defined by the placement suture 58 to couple the distal end 72 of the insertion tube 66 to the implant ball 40. Illustratively, the tube 66 may comprise a conventional feeding tube, a nasogastric (NG) tube, an endotracheal (ET) tube, or a Replogle tube. By pulling the free ends 76 of the placement suture 58, the ball 40 is coupled to the tube 66. As shown in FIG. 9, once the ball 40 is coupled to the distal end 72 of the tube 66, the tube 66 may be pushed through the oral cavity 20 to the proximal esophagus pouch 16.

Figure 10:
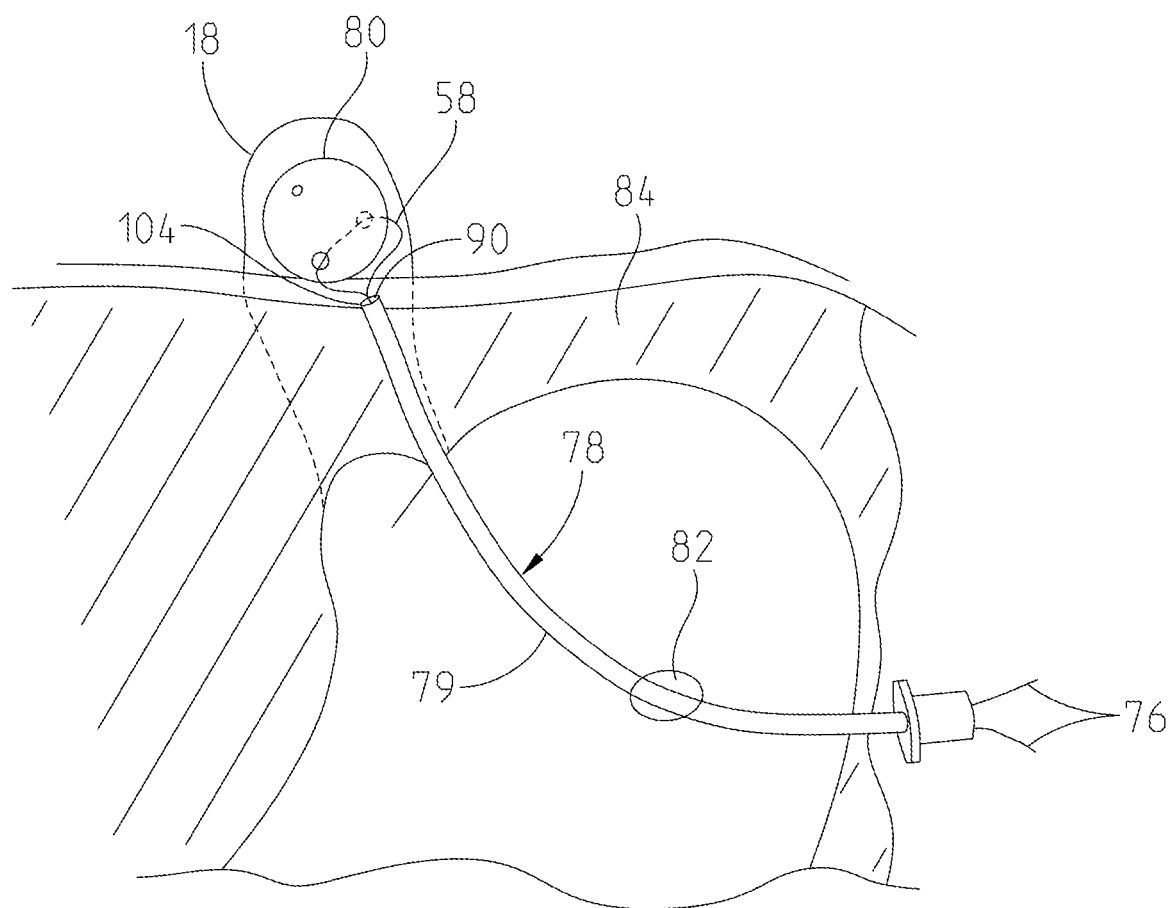
FIG. 10 is a perspective view, in partial and cross-section, showing the assembly of FIG. 8 received within the distal esophagus pouch.
Figure 11:
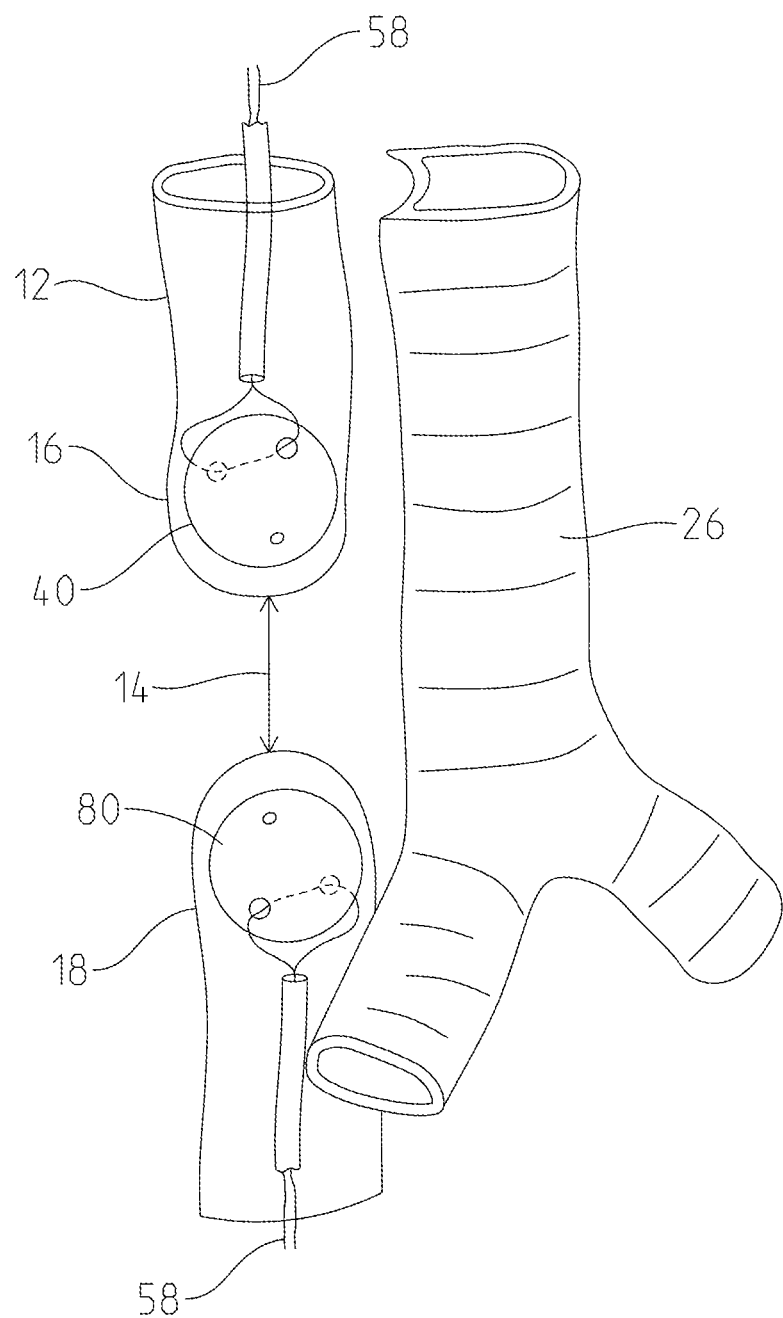
FIG. 11 is a perspective view showing the assembly of FIG. 8 received within the proximal esophagus pouch and the distal esophagus pouch.

As shown in FIG. 10, an insertion device 78, such as a gastrostomy tube 79, may be used to place a second or distal implant ball 80 into the distal esophagus pouch 18. More particularly, the tube 79 may be inserted through a gastrostomy hole 82 and diaphragm tissue or muscle 84, into the distal esophagus pouch 18. The distal implant ball 80 is substantially identical to the proximal implant ball 40.

Figure 12:
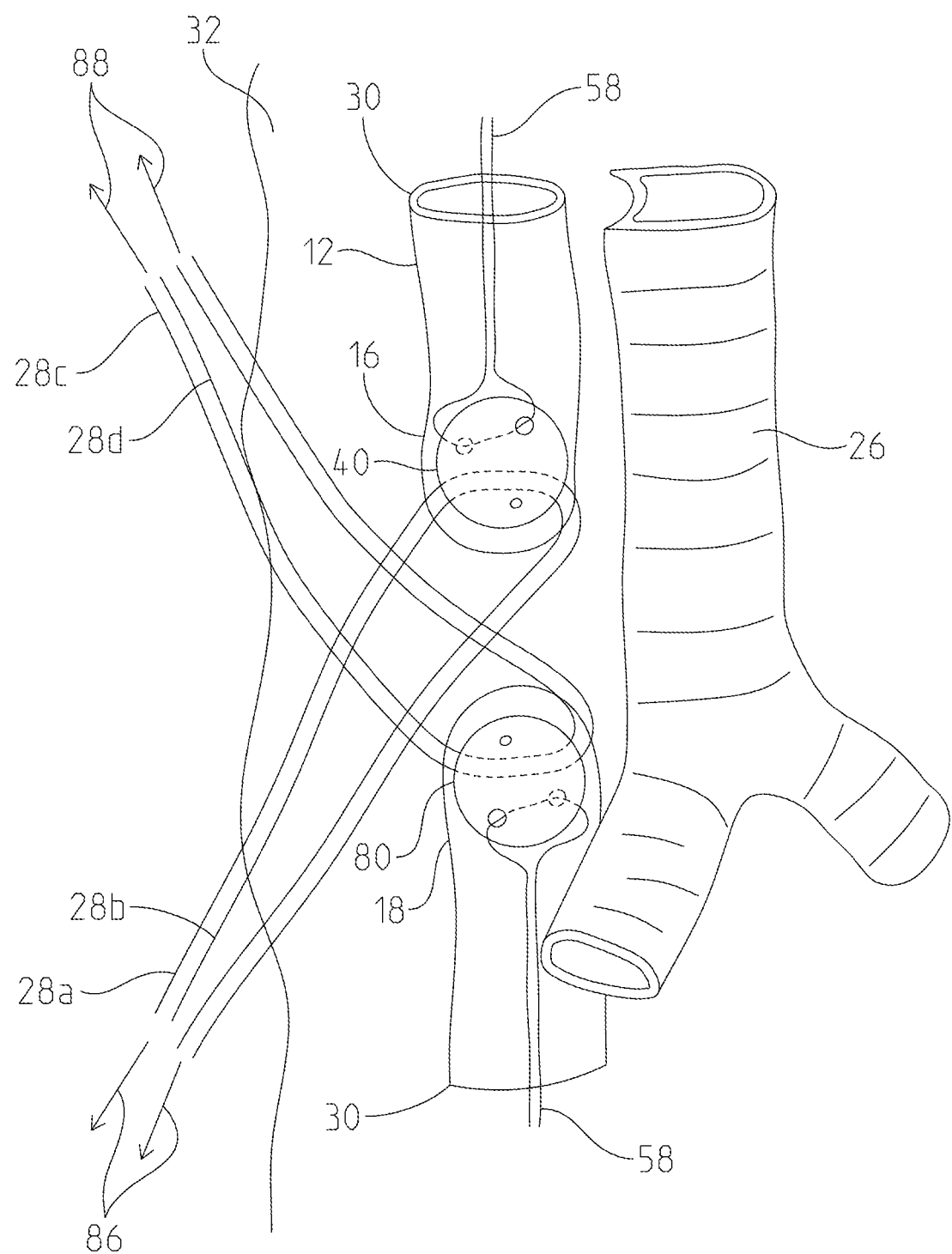
FIG. 12 is a perspective view similar to FIG. 11, showing tension sutures extending through the proximal and distal implant balls of FIG. 11 in an extra luminal configuration.

FIG. 12 illustrates an external traction configuration including both proximal ball 40 and distal implant ball 80. Once the proximal implant ball 40 is placed within the proximal esophagus pouch 16, the ball 40 is crossed by a conventional needle (not shown) with a first tension or traction suture 28a, and with a conventional needle (not shown) with a second tension or traction suture 28b. The sutures 28a and 28b are illustratively stretched out through incisions in the esophagus wall 30 and the thoracic wall 32. Once the tension sutures 28 are in place, the tube 66 can be removed. Alternatively, the tube 66 may remain in place.

Similarly, once the distal implant ball 80 is placed within the distal esophagus pouch 18, the ball 80 is crossed by a conventional needle (not shown) with a third tension or traction suture 28c, and a conventional needle (not shown) with a fourth tension or traction suture 28d. Once the tension sutures 28c and 28d are placed, the tube 79 can be removed. Alternatively, the tube 79 may remain in place.

The tension sutures 28a, 28b and 28c, 28d of FIG. 12 are illustratively stretched out through incisions in the esophagus wall 30 and the thoracic wall 32 in a crossing pattern. More particularly, the first and second tension sutures 28a, 28b extend in a distal (or downward) direction, and the third and fourth tension sutures 28c, 28d extend in a proximal (or upward) direction. Force applied to the sutures 28a, 28b in a distal direction (as shown by arrows 86 in FIG. 12) causes the proximal esophagus pouch 16 to lengthen or grow in a distal direction. Similarly, force applied to the sutures 28c, 28d in a distal direction (as shown by arrows 88 in FIG. 12) causes the distal esophagus pouch 18 to lengthen or grow in a proximal direction.

Figure 13:
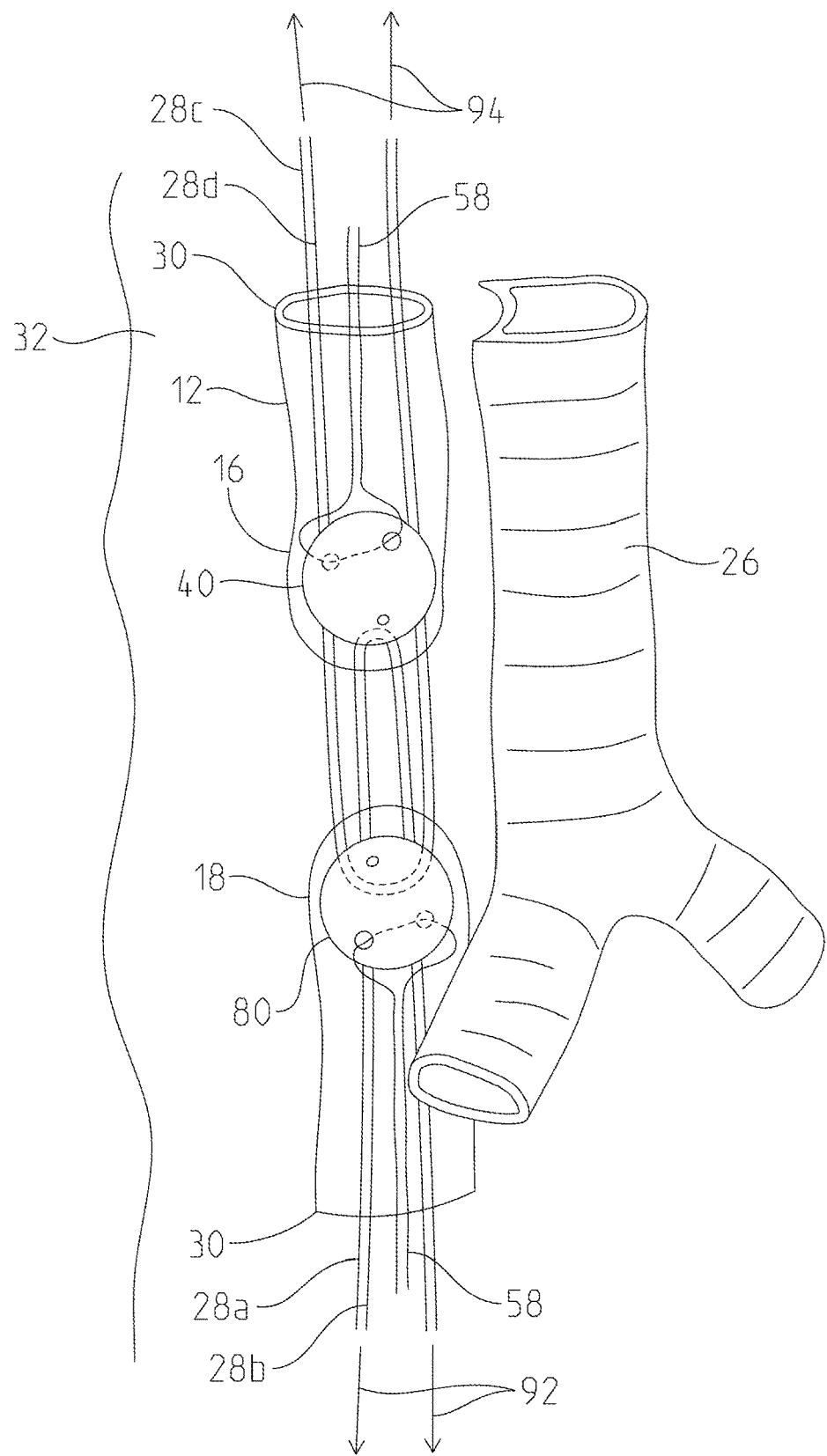
FIG. 13 is a further illustrative embodiment similar to FIG. 11, showing tension sutures extending through the proximal and distal implant balls of FIG. 11 in an intra luminal configuration.

FIG. 13 illustrates an internal traction configuration including both proximal implant ball 40 and distal implant ball 80. Once the proximal implant ball 40 is placed within the proximal esophagus pouch 16, the ball 40 is crossed by a conventional needle (not shown) with a first tension or traction suture 28a, and with a conventional needle (not shown) with a second tension or traction suture 28b. The sutures 28a and 28b are illustratively stretched out through the lumen 90 of the tube 79. Once the tension sutures 28 are in place, the tube 79 can be removed. Alternatively, the tube 79 may remain in place.

Similarly, once the distal implant ball 80 is placed within the distal esophagus pouch 18, the ball 80 is crossed by a conventional needle (not shown) with a third tension or traction suture 28c, and a conventional needle (not shown) with a fourth tension or traction suture 28d. The sutures 28c and 28d are illustratively stretched out through the lumen 68 of the tube 66. Once the tension sutures 28c and 28d are placed, the tube 66 can be removed. Alternatively, the tube 66 may remain in place.

The tension sutures 28a, 28b and 28c, 28d of FIG. 13 are illustratively stretched out through the lumens 68, 90 of the tubes 66, 79 in opposing directions. More particularly, the first and second tension sutures 28a, 28b extend in a distal (or downward) direction, and the third and fourth tension sutures 28c, 28d extend in a proximal (or upward) direction. Force applied to the sutures 28a, 28b in a distal direction (as shown by arrows 92 in FIG. 13) causes the proximal esophagus pouch 16 to lengthen or grow in a distal direction. Similarly, force applied to the sutures 28c, 28d in a distal direction (as shown by arrows 94 in FIG. 13) causes the distal esophagus pouch 18 to lengthen or grow in a proximal direction.

Figure 14:
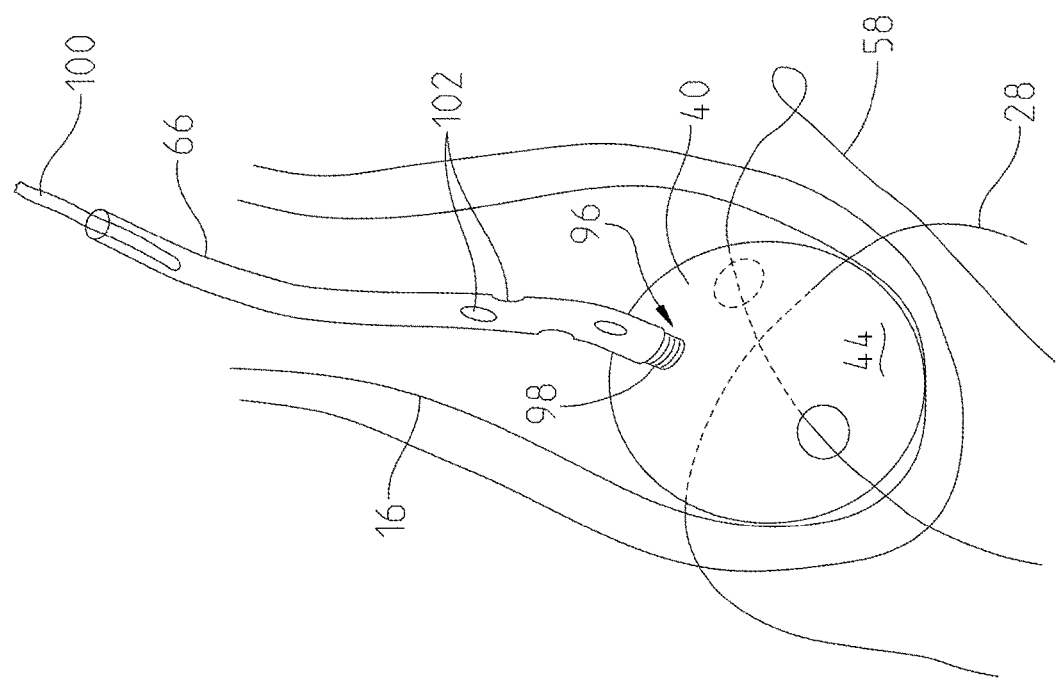
FIG. 14 illustrates a further illustrative coupling of the tube to the implant ball.

FIG. 14 illustrates a further illustrative coupler 96 for implant ball 40 defined by a threaded connection 98. Alternative couplers may include adhesives, bayonet connections, etc. A malleable wire 100 may be introduced into the insertion tube 66 to increase stiffness and facilitate introduction of the tube 66 in the esophagus 12. The tube 66 may include a plurality of orifices 102 to permit suction of saliva and esophageal pouch secretions. Adequate drainage of the proximal esophagus pouch 16 may be required to prevent saliva from spilling over in to the trachea 26, resulting in potential aspiration and/or pneumonia.

Figure 15:
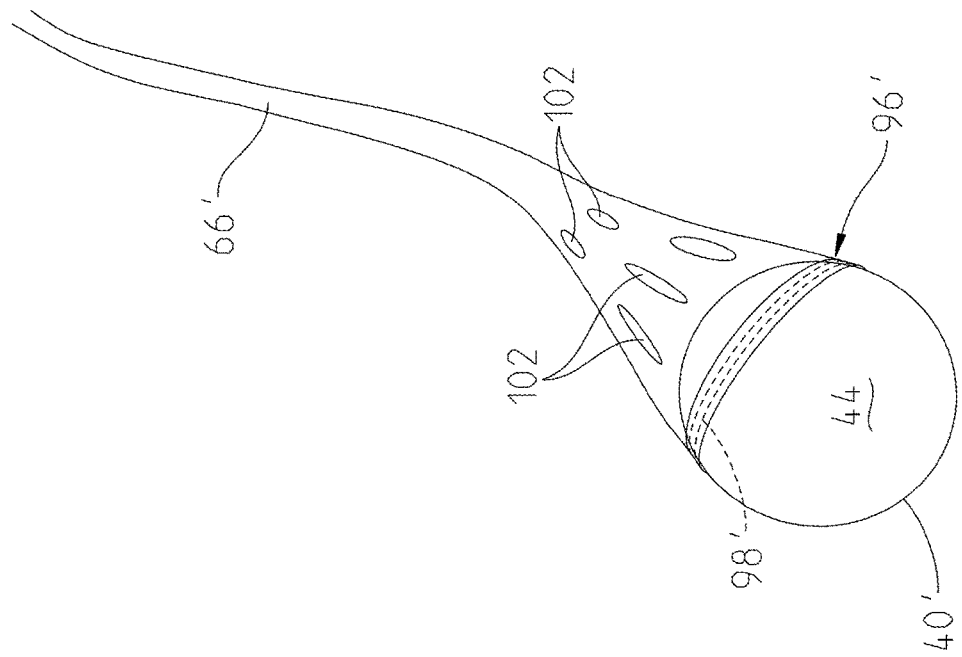
FIG. 15 illustrates further illustrative coupling of the tube to the implant ball.

FIG. 15 illustrates another illustrative implant ball 40' including an alternative coupler 96', illustratively a threaded connection 98' extending around the outer surface 44 of the ball 40. The tube 66' tapers inwardly from the threaded connection 98' to a reduced diameter portion of the tube 66'.

An illustrative method of lengthening the proximal esophagus pouch 16 begins by coupling the implant ball 40 to the distal end 72 of the insertion tube 66. More particularly, the placement suture 58 extends through the first opening 54, the internal chamber 46, and the second opening 56 of the ball 40. The placement sutures 28 are passed through the lumen 68 of the tube 66, and the free ends 76 pulled to secure the ball 40 to the distal end of the tube 66. The tube 66 is then passed through the oral cavity 20 of the patient 10 and into the esophagus 12 to place the ball 40 into the proximal esophagus pouch 16.

A needle is then used to pass the tension sutures 28 through the side wall 42 of the ball 40. The sutures 28 are illustratively stretched out through incisions in the esophagus wall 30 and the thoracic wall 32. Successive force is then applied to the ball 40 through the tension sutures 28 to elongate the proximal pouch 16 of the esophagus 12. Illustratively, the tension sutures 28 are gradually pulled out between 1 millimeter and 2 millimeters per day. After approximately two weeks, when the esophagus pouch 16 has stretched or grown to a sufficient length, surgeons perform another thoracotomy to connect the proximal and distal esophagus pouches 16 and 18 together.

In a further illustrative embodiment, lengthening the distal esophagus pouch 18 begins by coupling the implant ball 80 to the distal end 104 of the insertion tube 79. More particularly, the placement suture 58 extends through the first opening 54, the internal chamber 46, and the second opening 56 of the ball 80. The placement sutures 58 are passed through the lumen 90 of the tube 79, and the free ends 76 pulled to secure the ball 80 to the distal end 104 of the tube 79. The tube 79 is then passed through the gastrostomy hole 82 of the patient 10 and into the distal esophagus pouch 18. A needle is then used to pass the tension sutures 28 through the side wall 42 of the ball 80. The sutures 28 are illustratively stretched out through incisions in the esophagus wall 30 and the diaphragm muscle 84. Successive force is then applied to the ball 80 through the tension sutures 28 to elongate the distal pouch 18 of the esophagus 12. Illustratively, the tension sutures 28 are gradually pulled out between 1 millimeter and 2 millimeters per day. After approximately two weeks, when the esophagus pouch 18 has stretched or grown to a sufficient length, surgeons perform another thoracotomy to connect the proximal and distal esophagus pouches 16 and 18 together.

FIG. 3C shows an apparatus and method wherein tension sutures 28 are coupled to an inflatable balloon 106 disposed within the esophagus pouch 16. More particularly, the balloon 106 may comprises a Fogarty balloon placed within the esophagus pouch 16. A pinhole 108 is illustratively stabbed in the center of the pouch 16. The deflated balloon 106 is inserted into the pinhole 108 and then injected with water through a catheter (not shown). When the balloon is inflated, a few tensile sutures are sewn around the pinhole 108 so that the balloon 106 is not easily pulled out of the esophagus pouch 16.

Mechanical Test

Adult New Zealand white rabbits were chosen as an experimental animal to build an ex-vivo esophageal atresia model. After excising it from the rabbits, the middle of the folded esophagus was sewn together to make a pouch. Each folded esophagus was about 3.5 centimeters in length and 8 millimeters in width. This is considered similar to the esophagus size of a human neonate. The above detailed six suturing methods were then applied on these models.

To exert traction forces on the samples, the respective tension sutures 28 were hanged on an S-type hook. Moreover, a sine-wave shaped fixture was used to grip the esophageal pouch. The sine-wave shaped fixture was smooth enough to grip the esophageal pouch without damaging tissue. After the sample was settled on the machine, IRWIN® SL300 One Handed Bar Clamps was used to seal an acrylic box. Polybutylene succinate (PBS) was then poured into the acrylic box, which was then placed on a working platform until the entire sample was soaked in the solution.

A mechanical testing machine, illustratively Model 100R6 from Testresources, Inc., is used to stretch the tensile sutures at a rate of 10 millimeters per minute. The test was concluded when the sample was broken. The preload was 1 Newton, and the data recording started one the preload was reached.

In the experiment, three parameters were recorded including displacement, time to failure, and peak load. The recorded displacement was utilized to understand the differences of retaining distance between samples. Time was basically in direct proportion to displacement. Peak load was utilized to assess strength.

Statistical Analysis

Six groups including five samples each, for a total of 30 samples, were assessed in the study. Due to the relative small sample size, a non-parametric method was used to analyze the data. To compare the significant differences between the groups, each parameter was analyzed by Kruskal-Wallis test. If the difference was significant, the Mann-Whitney U test was utilized in the next step. IBM SPSS 22.0 software was used for this analysis.

Results

Table I below shows the average+/−standard deviation (SD) of each parameter in each group.

TABLE I

|  | Foker (FIG. 2A) | Purse (FIG. 2B) | Spiral (FIG. 2C) | Button (FIG. 3A) | Ball (FIG. 3B) | Balloon (FIG. 3C) |
| --- | --- | --- | --- | --- | --- | --- |
| Peak Load(N) | 9.31 ± 0.25 | 6.05 + 3.04 | 6.89 ± 2.24 | 4.13 ± 1.75 | 8.34 ± 1.59 | 4.52 ± 1.17 |
| Time(s) | 60.06 ± 19.54 | 66.01 ± 19.63 | 79.25 ± 16.39 | 73.873 ± 52.95 | 121.85 ± 13.5 | 123.06 ± 20.53 |
| Displacement (mm) | 9.71 ± 3.17 | 11 ± 3.27 | 13.2 ± 2.73 | 12.31 ± 8.82 | 20.3 ± 2.24 | 20.51 ± 3.43 |

The Kruskal-Wallis test showed that the differences in displacement, time and peak load were all significant among groups ($p<0.05$)

Mann-Whitney U test was done as a post-hoc test to identify which group was significantly different from the control group (i.e., the Foker technique of FIG. 2A). The adjustment for multiple comparisons was Least Significant Difference (LSD) due to small sample size. The significant level was set at $p<0.05$. Table II below lists the P-value of the Mann-Whitney U test (*: $p<0.05$).

TABLE II

| Groups | Peak load | Displacement | Time |
| --- | --- | --- | --- |
| Purse (FIG. 2B) | 0.690 | 0.690 | 0.841 |
| Spiral (FIG. 2C) | 0.095 | 0.151 | 0.222 |
| Button (FIG. 3A) | 0.008* | 1.000 | 1.000 |
| Ball (FIG. 3B) | 0.032* | 0.008* | 0.008* |
| Balloon (FIG. 3C) | 0.008* | 0.008* | 0.008* |

Figure 16:
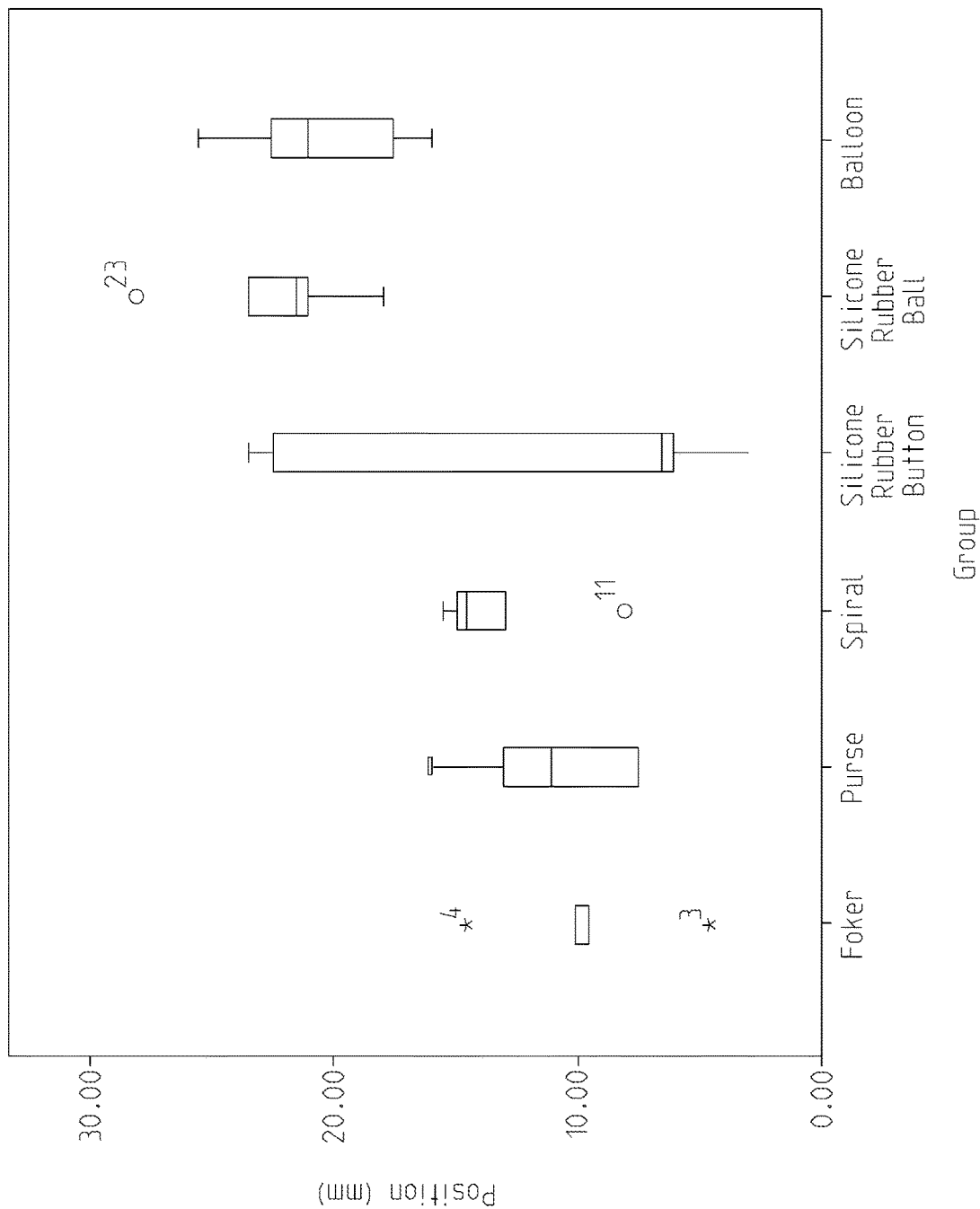
FIG. 16 is a first chart of illustrative displacements of the traction methods of FIGS. 2A-3C.
Figure 17:
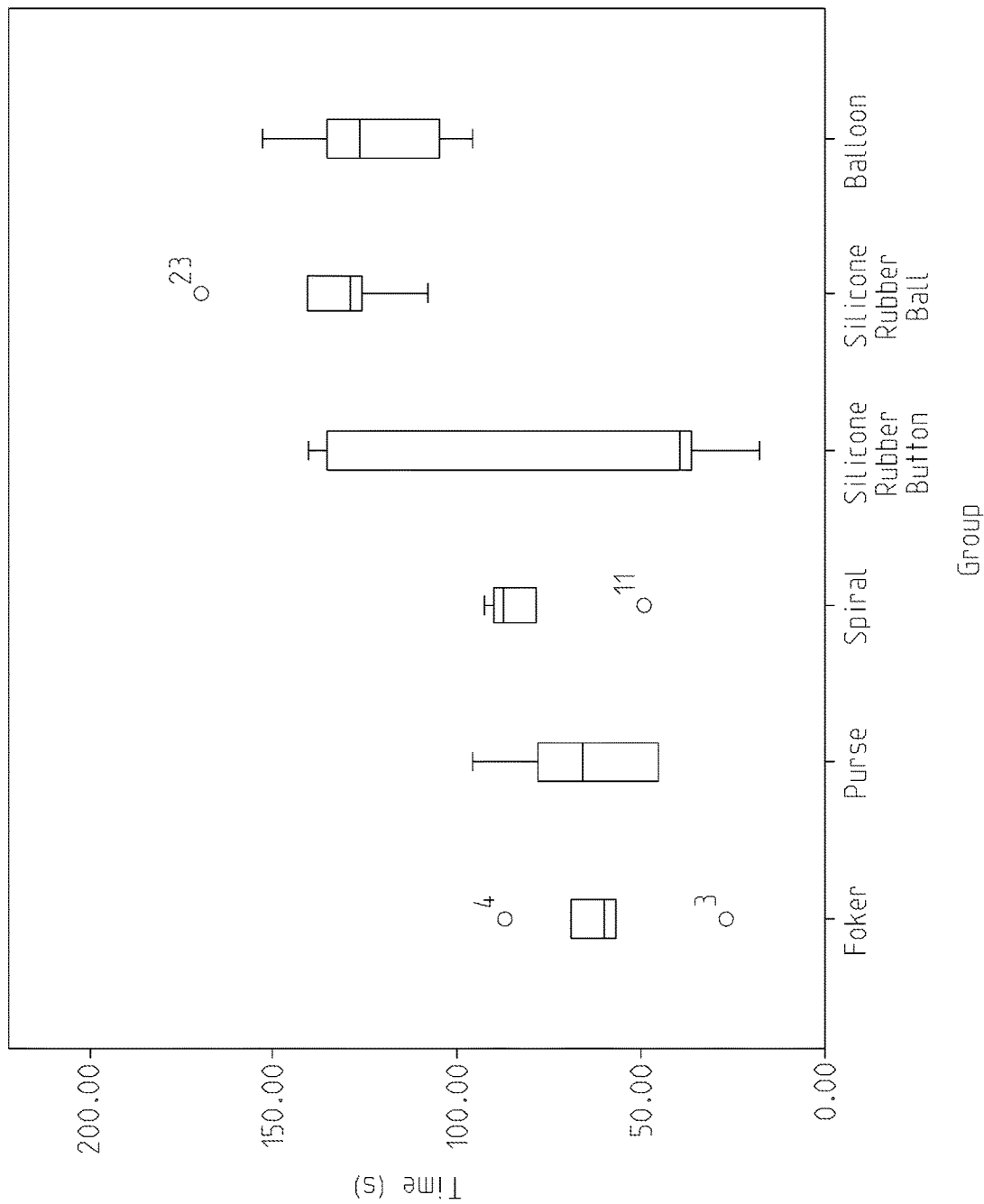
FIG. 17 is a second chart of illustrative times of the traction methods of FIGS. 2A-3C.
Figure 18:
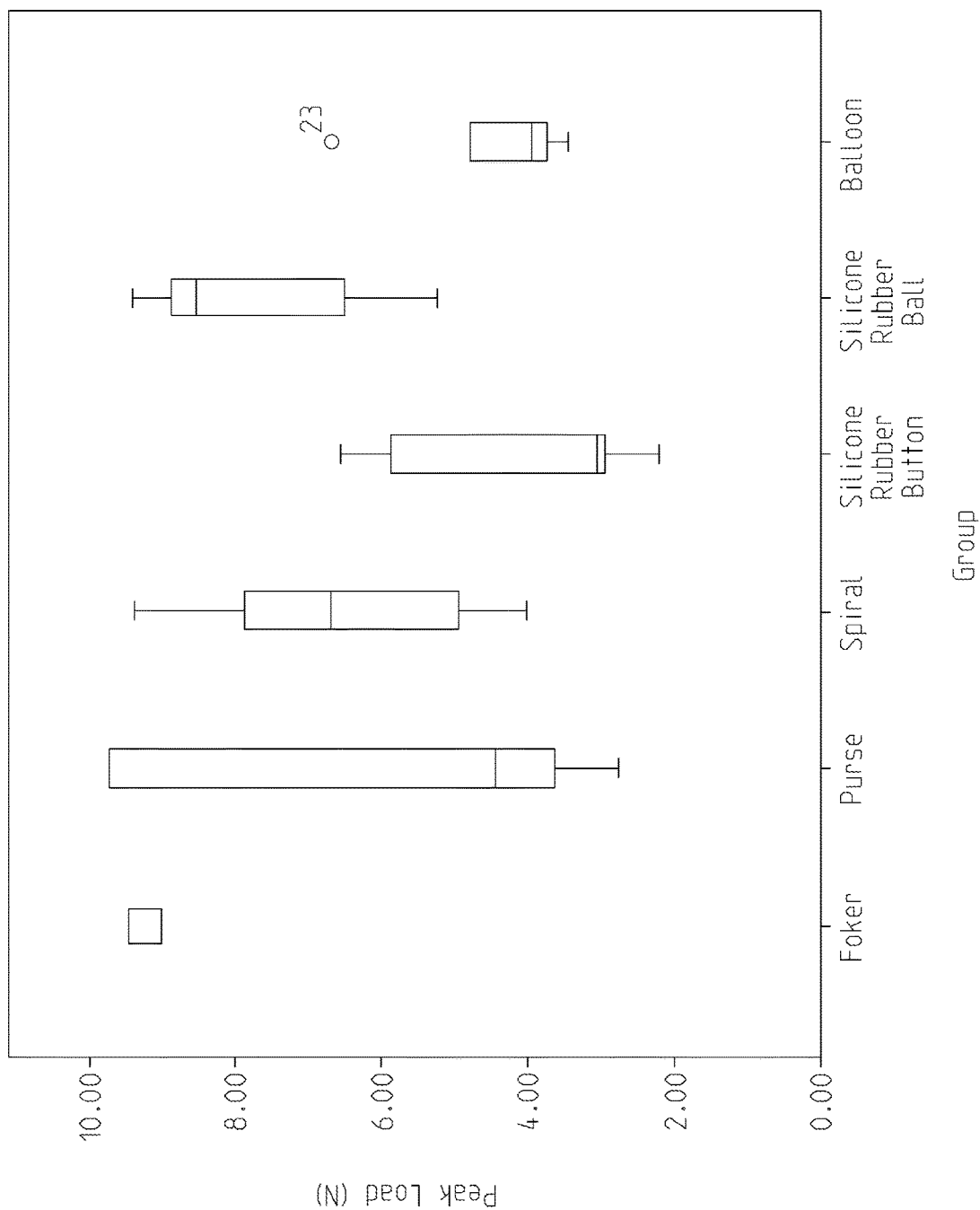
FIG. 18 is a third chart of illustrative peak loads of the traction methods of FIGS. 2A-3C.

With reference to FIGS. 16-18, compared to the control group (i.e., the Foker technique), significant differences were found in the peak load of the silicone button and the Fogarty balloon, and in displacement and time of the silicone ball and the Fogarty balloon.

The displacements of silicone ball 40 and the Fogarty balloon 106 groups were significantly higher than that of the control group. Since all the samples were tested in displacement control, time was direct proportional to displacement. The results of time to failure were quite similar as the results of displacement. The results of both parameters in silicone ball 40 group and Fogarty balloon 106 group were significantly higher than that of the control group. Peak load was opposite to our expectation. The control group showed significantly higher peak load than the silicone button 36 group, Fogarty balloon 106 group, and silicone ball 40 group. From the boxplots we can find that control group was also higher than every other group, and the standard deviation is smallest as well.

Compared to the control group, significant differences were found in the peak load of the silicone button 36 and the Fogarty balloon 106. Also, significant differences were found in displacement and time of the silicone ball 40 and the Fogarty balloon 106. The displacements of the silicone ball 40 and the Fogarty balloon 106 groups were significantly higher than that of the control group.

Peak load was opposite to expectations. The control group showed significantly higher peak load than the silicone button 36 group, the Fogarty balloon 106, and the silicone ball 40.

The spiral method was acceptable, but did not show better performance than control. Otherwise, using the purse string, button, and balloon methods to elongate the pouch in LGEA might lead to unsatisfactory outcomes. Overall, the ball method was considered to be the preferred choice. It affords larger displacement as well as retain longer pulling time, and the peak load is also large enough to bear the loading in clinical setting.

Although the invention has been described in detailed with reference to preferred embodiments, variations and modifications exist within the spirit and scope of the invention as described and defined in the following claims.

The invention claimed is:

1. A system for lengthening a tubular organ by applying tensile force, the system comprising:
a first implant configured to be received within a first pouch of the tubular organ, the first implant comprising a ball including an internal chamber and a spherical outer surface;
a first tension suture extending through the first implant;
an insertion device for placing the first implant within the first pouch, the insertion device including a proximal end and a distal end;
a coupler for releasably coupling the first implant to the distal end of the insertion device;
wherein tensile force applied to the first tension suture results in a semispherical distribution of force by the ball causing the first pouch to elongate;
wherein the insertion device comprises a tube including a lumen extending longitudinally between the proximal end and the distal end, and the coupler comprises a placement suture extending through the lumen of the tube; and
wherein the first implant includes a first opening and a second opening in spaced relation to the first opening, the placement suture extending through the first opening and the second opening.

2. The system of claim 1, wherein the implant includes a marker element for at least one of radiology and ultrasonic detection.

3. The system of claim 2, wherein the marker element is a radiopaque element including at least one of an internal radiopaque particle, and a radiopaque substance coating.

4. The system of claim 1, wherein the insertion device comprises a Replogle tube including at least one drainage opening configured to drain saliva.

5. The system of claim 4, further comprising a malleable wire configured to be inserted within the lumen of the Replogle tube for facilitating placement.

6. The system of claim 1, wherein the ball of the first implant includes a side wall defining the internal chamber.

7. The system of claim 6, wherein the ball is formed of a polymer and has an outer diameter of between 5 millimeters and 10 millimeters.

8. The system of claim 1, further comprising:
a second implant configured to be received within a second pouch of the tubular organ, the second implant including an arcuate outer surface; and
a second tension suture extending through the second implant;
wherein tensile force applied to the first tension suture and the second tension suture cause the first pouch and the second pouch to elongate toward each other.

9. The system of claim 1, wherein the tension suture provides external traction by extending through tissue adjacent the organ.

10. The system of claim 1, wherein the tension suture provides internal traction by extending through the insertion device.

11. An implant for lengthening a tubular organ by applying tensile force, the implant comprising:
a ball including a side wall defining an internal chamber and a spherical outer surface, the ball being formed of a polymer and having a fixed outer diameter of between 5 millimeters and 15 millimeters; and
a tension suture extending through a first location in the side wall of the ball, the internal chamber of the ball, and a second location in the side wall of the ball, wherein tensile force applied to the tension suture causes a semi-spherical distribution of force by the ball to a tubular organ for lengthening the tubular organ.

12. The implant of claim 11, wherein the ball has a fixed outer diameter of between 8 millimeters and 10 millimeters.

13. The implant of claim 11, further comprising a coupler for releasably coupling the implant to an insertion device.

14. The implant of claim 11, wherein the ball includes a marker element for at least one of radiology and ultrasonic detection.

15. The implant of claim 14, wherein the marker element is a radiopaque element including at least one of an internal radiopaque particle, and a radiopaque substance coating.

16. The implant of claim 11, further comprising a placement suture, wherein the ball includes a first opening and a second opening in spaced relation to the first opening, the placement suture extending through the first opening, the internal chamber and the second opening.

17. A system for lengthening a tubular organ by applying tensile force, the system comprising:
a first implant configured to be received within a first pouch of the tubular organ, the first implant comprising a first ball including a spherical outer surface;
a first tension suture extending through the first implant in a distal direction;
wherein tensile force applied to the first tension suture results in a semispherical distribution of force by the first ball causing the first pouch to elongate;

a second implant configured to be received within a second pouch of the tubular organ, the second implant comprising a second ball including a spherical outer surface;

a second tension suture extending through the second implant in a proximal direction; and wherein tensile force applied to the second tension suture results in a semispherical distribution of force by the second ball causing the second pouch to elongate toward the first pouch.

18. The system of claim 17, further comprising:

an insertion device for placing the first implant within the first pouch, the insertion device including a proximal end and a distal end; and a coupler for releasably coupling the first implant to the distal end of the insertion device.

19. The system of claim 18, wherein the insertion device comprises a tube including a lumen extending longitudinally between the proximal end and the distal end, and the coupler comprises a placement suture extending through the lumen of the tube.

20. The system of claim 19, wherein the first implant includes a first opening and a second opening in spaced relation to the first opening, the placement suture extending through the first opening and the second opening.

21. The system of claim 18, wherein the insertion device comprises a tube, and the coupler comprises a threaded connection between the first implant and the tube.

22. The system of claim 18, wherein the insertion device comprises a Replogle tube including at least one drainage opening configured to drain saliva.

23. The system of claim 17, wherein the first ball of the first implant includes a side wall defining an internal chamber.

24. The system of claim 23, wherein the first ball is formed of a polymer and has an outer diameter of between 5 millimeters and 10 millimeters.

* * * * *